United States Patent [19]
Cho et al.

[11] Patent Number: 5,834,017
[45] Date of Patent: *Nov. 10, 1998

[54] ORAL CYCLOPSPORIN FORMULATIONS

[75] Inventors: Moo J. Cho, Chapel Hill, N.C.; Ralph F. Levy, Pleasanton; Philippe J. Pouletty, Atherton, both of Calif.

[73] Assignee: SangStat Medical Corporation, Menlo Park, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 519,689

[22] Filed: Aug. 25, 1995

[51] Int. Cl.⁶ .............................. A61K 9/10; A61K 9/48
[52] U.S. Cl. .................. 424/455; 514/885; 514/962; 514/937; 514/975
[58] Field of Search .................. 424/456, 455; 514/885, 962, 975, 937

[56] References Cited

U.S. PATENT DOCUMENTS

| | | | |
|---|---|---|---|
| 506,219 | 4/1893 | Desai | 514/3 |
| 4,117,118 | 9/1978 | Harri et al. | 424/177 |
| 4,220,641 | 9/1980 | Traber et al. | 424/177 |
| 4,388,307 | 6/1983 | Cavanak | 424/177 |
| 4,792,449 | 12/1988 | Ausman et al. | 424/440 |
| 4,889,723 | 12/1989 | Kim et al. | 424/450 |
| 4,970,076 | 11/1990 | Horrobin | 424/456 |
| 4,990,337 | 2/1991 | Kurihara et al. | 424/427 |
| 4,996,193 | 2/1991 | Hewitt et al. | 514/11 |
| 5,047,396 | 9/1991 | Orban et al. | 514/11 |
| 5,051,402 | 9/1991 | Kurihara et al. | 514/11 |
| 5,118,493 | 6/1992 | Kelley et al. | 424/10 |
| 5,154,930 | 10/1992 | Popescu et al. | 424/489 |
| 5,342,625 | 8/1994 | Hauer et al. | 424/455 |
| 5,350,741 | 9/1994 | Takada | 514/3 |
| 5,364,632 | 11/1994 | Benita et al. | 424/450 |

FOREIGN PATENT DOCUMENTS

| | | |
|---|---|---|
| 2009533 | 9/1990 | Canada . |
| 1326995 | 2/1994 | Canada . |
| 2106827 | 3/1994 | Canada . |
| 0 572 942 A2 | 12/1993 | European Pat. Off. . |
| 0 589 843 | 3/1994 | European Pat. Off. . |
| 0 650 721 A1 | 5/1995 | European Pat. Off. . |
| 43 40 781 | 6/1995 | Germany . |
| 195 39 860 | 5/1996 | Germany . |
| 2 015 339 | 9/1979 | United Kingdom . |
| 2 200 048 | 7/1988 | United Kingdom . |
| 2 209 671 | 5/1989 | United Kingdom . |
| 2 221 157 | 1/1990 | United Kingdom . |
| 2 224 205 | 5/1990 | United Kingdom . |
| 2 228 198 | 8/1990 | United Kingdom . |
| WO 91/16057 | 10/1991 | WIPO . |
| WO 92/09299 | 6/1992 | WIPO . |
| WO 92/18105 | 10/1992 | WIPO . |
| WO 93/00106 | 1/1993 | WIPO . |
| WO 93/23010 | 11/1993 | WIPO . |
| WO 94/23733 | 10/1994 | WIPO . |
| WO 95/06464 | 3/1995 | WIPO . |

OTHER PUBLICATIONS

Tarr & Yalkowsky, "Enhanced Intestinal Absorption of Cyclosporine in Rats Through the Reduction of Emulsion Droplet Size", Pharmaceutical Research (1989), 6:40–43.

Abdallah and Mayersohn, "The Preparation and Evaluation of a Tablet Dosage Form of Cyclosporine in Dogs", Pharmaceutical Research (1991), 8:518–522.

(List continued on next page.)

*Primary Examiner*—Edward J. Webman
*Attorney, Agent, or Firm*—Flehr Honbach Test Albritton & Herbert LLP; Richard F. Trecartin; Mark T. Kresnak

[57] ABSTRACT

Improved oral cyclosporin formulations which have high bioavailability and are capable of administration in hard capsules, are provided. In the subject formulations, cyclosporin is delivered in an orally acceptable vehicle comprising at least one alkanol of from 2 to 3 carbon atoms in combination with at least one non-ionic surfactant and an ester of an alcohol and a fatty acid having a hydrocarbon chain of from 14 to 18 carbon atoms. The subject formulations find use in immunosuppressive therapy.

20 Claims, 2 Drawing Sheets

FORMULATION

OTHER PUBLICATIONS

Sato et al., "Enhancement of The Intestinal Absorption of Cyclosporine Derivative by Milk Fat Globule Membrane", Biol. Pharm. Bull. 17:1526–1528.

Benmoussa et al., "Cyclosporin Absorption Is Impaired by the Fat Substitutes, Sucrose Polyester and Tricarballylate Triester, in the Rate", Pharmaceutical Research (1994), 11:1458–1461.

Trull et al., "Cyclosporin Absorption From Microemulsion Formulation in Liver Transplant Recipient", The Lancet (1993), 341:433.

Ferrea et al., "Oral Microemulsion Formulation Substitutes for Intravaneous Cyclosporin in Child with Graft–Versus–Host–Disease", The Lancet (1994), 344:480–481.

Reymond et al., "In Vivo Model for Ciclosporin Intestinal Absorption in Lipid Vehicles", Pharmaceutical Research (1988), 5:677–679.

Ritschel et la., "Improvement of Peroral Absorption of Cyclosporine A By Microemulsion", Meth. Find Exp. Clin. Pharmacol. (1990), 12:127–134.

Reymond and Sucker, "In Vitro Model for Ciclosporin Intestinal Absorption in Lipid Vehicles", Pharmaceutical Research (1988), 5:673–676.

Cavanak and Sucker, "Formulation of Dosage Forms", Prog. Allergy (1986), 38:65–72.

ORAL CYCLOPSPORIN FORMULATIONS

FIELD OF THE INVENTION

The field of this invention is oral cyclosporin formulations.

BACKGROUND

Despite efforts to avoid graft rejection through host-donor tissue type matching, in the majority of transplantation procedures where a donor organ is introduced into a host, immunosuppressive therapy is critical to the maintained viability of the donor organ in the host. A variety of immunosuppressive agents have been employed in transplantation procedures, including azathioprine, methotrexate, cyclophosphamide, FK-506, rapamycin and corticosteroids. Agents finding increasing use in immunosuppressive therapy due to their preferential effect on T-cell mediated reactions are the cyclosporins.

Cyclosporins are a class of cyclic polypeptides consisting of eleven amino acids which are produced as a metabolite by the fungus species Tolypocladium inflatum Gams. Cyclosporins have been observed to reversibly inhibit immunocompetent lymphocytes, particularly T-lymphocytes, in the $G_0$ or $G_1$ phase of the cell cycle. Cyclosporins have also been observed to reversibly inhibit lymphokine production and release. Although a number of cyclosporins are known, Cyclosporin A is the most widely used.

Use of Cyclosporin A has been reported to prolong the survival of allogeneic transplants involving skin, heart, kidney, pancreas, bone marrow, small intestine and lung. In allogeneic transplantations, Cyclosporin A has been shown to suppress humoral immunity and, to a greater extent, cell mediated immune reactions, including: allograft rejection, delayed hypersensitivity, experimental allergic encephalomyelitis, Freund's adjuvant arthritis, and graft vs. host disease. Although success has been realized with Cyclosporin A, following transplantation administration of the agent must be continued since the benefits of cyclosporin therapy are reversible and graft rejection occurs once administration of Cyclosporin A is discontinued.

Although cyclosporin formulations for both oral and intravenous administration have been developed, because of the ease of administration and greater patient acceptance, oral administration of cyclosporin is preferred. Furthermore, intravenous administration of cyclosporin can result in anaphylactic reactions, a side effect not observed with oral formulations. Oral cyclosporin formulations which have been developed and are currently marketed include both soft gelatin capsule and solution formulations, both of which are sold under the trademark SANDIMMUNE®.

In using oral cyclosporin formulations in immunosuppressive therapy, both the care giver and manufacturer must be cognizant of many issues. With oral cyclosporin formulations, cyclosporin bioavailability can be limited because of cyclosporin's immiscibility in water and the tendency of cyclosporin to precipitate in aqueous environments. In addition, the concentration of cyclosporin present in oral formulations can be limited due to cyclosporin's hydrophobic nature. Furthermore, cyclosporin absorption by the gastrointestinal tract can be erratic from one formulation batch to the next, requiring constant monitoring of cyclosporin blood levels during treatment. Finally, packaging and storage stability are an issue with oral formulations. For example, with soft gelatin capsule formulations of cyclosporin, air tight packaging must be employed, which is inconvenient due to bulkiness and high cost.

Thus, desirable oral cyclosporin formulations would be formulations that address at least some of the above issues. Ideally, oral formulations would promote high bioavailability, comprise high concentrations of cyclosporin and would be amenable to preparation in hard capsule form.

Relevant Literature

Physician's Desk Reference (1994) pp 2071–2074 describes oral cyclosporin formulations currently sold under the trademark SANDIMMUNE®.

U.S. Patents of interest describing cyclosporins and derivatives thereof include: U.S. Pat. Nos. 4,220,641; 4,639,434; 4,289,851; and 4,384,996. U.S. Pat. No. 5,047,396 describes an intravenous preparation for administration of cyclosporin. U.S. Pat. Nos. 4,388,307; 4,970,076 and 4,990,337 describe the preparation of oral cyclosporin formulations.

The preparation of hard capsules for the oral delivery of pharmaceutical formulations is described in U.S. Pat. Nos. 4,822,618; 4,576,284; 5,120,710; and 4,894,235.

SUMMARY OF THE INVENTION

Oral cyclosporin formulations, and methods for their use in immunosuppressive therapy, are provided. The subject formulations comprise cyclosporin in an orally acceptable vehicle comprising at least one alkanol of from 2 to 3 carbon atoms and at least one non-ionic surfactant in combination with fatty acid esters in which the acyl group contains a hydrocarbon chain of from 14 to 18 carbon atoms. The cyclosporin formulations can be packaged as hard capsules.

DESCRIPTION OF THE SPECIFIC EMBODIMENTS

Figure 1:
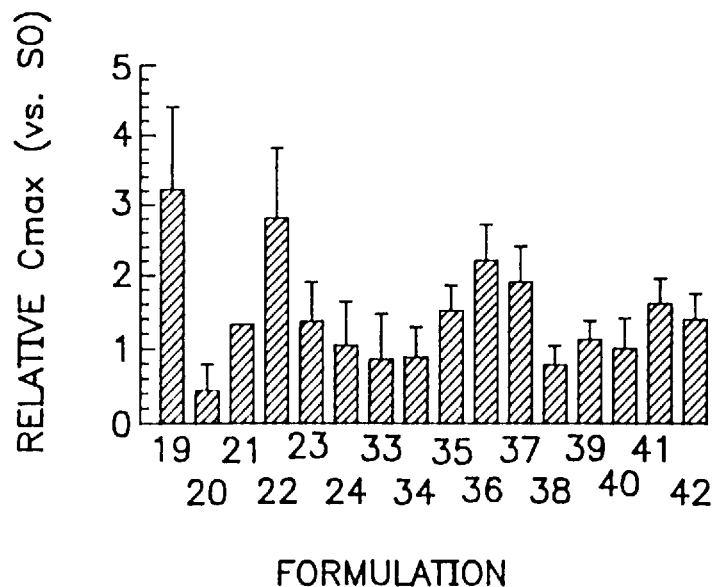
FIG. 1 provides the cyclosporin peak concentration ($C_{max}$) achieved in rats for several oral formulations according to the subject invention, where the $C_{max}$ is shown as a relative value compared to the $C_{max}$ achieved with SANDIMMUNE ORAL formulation (SO).

Oral cyclosporin formulations are provided which can be formulated as capsules, particularly hard capsules, and promote bioavailability. In the subject formulations, cyclosporin is present in an orally acceptable vehicle comprising at least one alkanol of from 2 to 3 carbon atoms in combination, at least one non-ionic surfactant, and an ester of a fatty acid having a hydrocarbon chain of from 14 to 18 carbon atoms. In addition to providing for high bioavailability, the subject formulations provide for reproducible cyclosporin absorption from one batch of a formulation to the next. The subject formulations find use in immunosuppressive therapy.

A number of cyclosporins are known in the art to exhibit immunosuppressive activity and may be delivered in the subject oral formulations. Cyclosporins that may be administered in the subject formulations include Cyclosporin A, Cyclosporin B, Cyclosporin C, Cyclosporin D and Cyclosporin G, as well as synthetic analogs thereof See Merck Index (1989) 2759. The subject oral formulations are particularly suited for the delivery of Cyclosporin A. When delivered in the subject formulations, Cyclosporin A will be present in concentrations ranging from 50 to 150 mg/ml, usually 100 to 150 mg/ml, based on the volume of the vehicle component of the formulation.

The vehicle component of the subject formulation will include at least one alkanol, usually not more than two alkanols, where the alkanol will usually be from 2 to 3 carbon atoms, and have not more than 1 hydroxy group per 1.5 carbon atoms. The alkanol may have 1 to 2 hydroxyl groups. Suitable alkanols include ethanol and propylene glycol. The total amount of alkanol in the formulation will range from 5 to 35%, usually from about 5 to 30% (v/v) of the formulation. When present, the amount of ethanol in the subject formulation will range from 5 to 15%, usually from about 5 to 10% (v/v) of the formulation. The amount of propylene glycol, when present, will range from 5 to 35%, usually from about 10 to 30% (v/v) of the formulation.

Also present in the orally acceptable vehicle will be at least one non-ionic polyoxyalkylene surfactant, usually not more than two polyoxyalkylene non-ionic surfactants. The polyoxyalkylene surfactants will have a hydrophilic-lipophilic-balance (HLB) of from about 5 to 20, usually from about 8 to 16. Preferably, the polyoxyalkylene non-ionic surfactants employed in the subject formulations will be polyoxyethylene compounds. Polyoxyethylene compounds include: ethoxlyated alcohols, i.e. polyoxyethylene alcohols or ethoxylated fatty alcohols, generally of from 10 to 18, usually from 10 to 14 carbon atoms, as well as ether and ester substituents thereof; and fatty acid monoesters of ethoxylated polyols of from 4 to 6 carbon atoms, usually 6 carbon atoms, e.g. sorbitol. The number of ethylenoxy groups will generally be in the range of 2 to 30, usually in the range from about 2 to 25. Preferred surfactants are polyoxyethylene (4) lauryl ether (BRIJ 30®) and polyoxyethylene (20) mono sorbitan mono-oleate (TWEEN 80®). The total amount of non-ionic surfactants present in the subject formulations will range from 5 to 50%, usually from about 10 to 40% (v/v) of the formulation. Where TWEEN 80® is present in the formulation, it will usually be present in amounts ranging from 5 to 50%, more usually from about 20 to 30% (v/v) of the formulation. When BRU 30® is present in the subject formulation, it will usually be present in amounts ranging from 10 to 45%, more usually from about 15 to 40% (v/v) of the formulation.

In the subject formulations, in combination with the alkanol and non-ionic surfactant will be an ester of a fatty acid, where the hydrocarbon chain of the fatty acid will be from 14 to 18 carbon atoms in length and will generally be an even numbered chain, where the hydrocarbon chain may be saturated or unsaturated, usually of not more than two sites of unsaturation. Fatty acids of interest will generally be of plant or mammalian origin and include palmitate, stearate, palmitoleate, linoleate, linolineate and the like, particularly myristate and oleate. The alcohol of the fatty acid ester will be a lower alkanol of from 2 to 4 carbon atoms in length, usually 2 to 3 carbon atoms in length, with or without branches. Fatty acid esters of particular interest are isopropyl myristate and ethyl oleate. The fatty acid ester component of the subject formulations will make up from about 35 to 80% (v/v) of the formulation, where isopropyl myristate, when present, will range from about 55 to 75% (v/v), and ethyl oleate, when present, will range from about 35 to 75% (v/v) of the total formulation. Usually the fatty acid ester will be present in an amount at least about equal (v/v) and up to 8 times the amount of surfactant in the formulation, usually not greater than 5 times the amount of surfactant in the formulation (v/v).

Optionally, the subject formulations may comprise a polyethylene glycol, usually polyethylene glycol 200 to 400. Polyethylene glycol, when included in the subject formulations, will be present in amounts ranging from 5 to 15%, usually 5 to 10% (v/v) of the formulation.

In some instances, it is found that an ester of a fatty acid is not essential to the formulation. In such instances, the formulation will comprise ethanol and propylene glycol in combination with a polyoxyalkylene non-ionic surfactant. In such formulations, the amount of ethanol will range from about 5 to 15% (v/v), usually from about 5 to 10% (v/v), while the amount of propylene glycol will range from about 40 to 55% (v/v), usually from about 45 to 50% of the formulation. The formulation will comprise at least one non-ionic polyoxyethylene surfactant, wherein said surfactant is selected from the group consisting of polyoxyethylene ethers and fatty acid monoesters of ethoxylated polyols of from 4 to 6 carbon atoms, e.g. polyoxyethylene (20) mono sorbitan mono-oleate, and will be present in said formulation in an amount ranging from 40 to 55% (v/v), usually from about 45 to 50% (v/v) of the formulation.

Of particular interest are formulations in which the non-ionic surfactant is a fatty acid monoester of sorbitol, where the ratio of fatty acid ester to surfactant in the formulation ranges from about 1.5 to 2.5, and is usually about 2. Formulations which are less preferred are those formulations comprising polyoxyethylene (4) lauryl ether as the non-ionic surfactant and isopropyl myristate as the fatty acid ester, where the ratio of fatty acid ester to surfactant in the formulation is in excess of about 1.5.

Also present in the subject formulations may be a number of minor components which provide various functions, such as enzyme inhibitors, preservatives, antioxidants, antimicrobial agents, stabilizers and the like. The total amount of these additives, when present in the formulation, will normally not be greater than 5 weight % of the formulation. A number of excipients may also be present in the subject formulations, as is known in the art.

The subject formulations are suitable for administration in capsule form, e.g. hard and soft capsules. Methods of producing hard capsules comprising liquid formulations are known in the art and described in U.S. Pat. Nos. 4,822,618 and 4,576,284, the disclosures of which are herein incorporated by reference. Generally, hard capsules that find use with the subject formulations will comprise two parts: a shell component and a cap component. The shell and cap components fit together to produce an enclosed cavity of defined volume sealed in a hard capsule shell. The shell and cap components may be fabricated from a hydrophilic polymer, such as starch or gelatin. In preparing the hard capsules, the liquid formulation will be poured into the shell component and then the capsule will be sealed by fitting the cap component over the shell component. The seal between the two components may be secured, thereby preventing leakage of the enclosed formulation from the capsule, by using a sealant as described in EP 116744, the disclosure of which is herein incorporated by reference. To avoid degradation in the stomach, capsules comprising the subject formulations may be coated with an enteric coating which inhibits degradation of the capsule in the acidic environment of the stomach. A variety of enteric coatings are known in the art. See for example, U.S. Pat. No. 5,206,219, the disclosure of which is herein incorporated by reference.

The subject formulations find use in immunosuppressive therapy. Immunosuppressive therapy is indicated in a wide variety of diseases, including idiopathic nephrotic syndrome, type I insulin-dependent diabetes, Behcet's syndrome, active Crohn's disease, aplastic anemia, severe corticosteroid-dependent asthma, psoriasis and other diseases where the immune system may play a pathogenic role. Of particular interest is the use of the subject formulations in transplant situations, including both allogeneic and xenogeneic organ, tissue or cell transplantation, where immunosuppression is desired to ensure maintained viability of the transplanted organ or tissue or cell following transplantation, i.e. to prevent graft rejection or prevent graft vs. host disease, e.g. following bone marrow transplantation.

In using the subject formulations to provide immunosuppressive therapy to a host, an effective amount of cyclosporin will be orally administered to achieve the desired level of immunosuppression in the host, depending on the particular condition to be treated. With transplantation, usually an initial dosage of cyclosporin will be administered prior to operation. Following transplantation of the donor organ to the host, the cyclosporin will be administered repeatedly, i.e. chronically, to the host to maintain immunosuppression. The initial dosage will be administered 4 to 12 hours prior to transplantation and may range from 10 to 18 mg/kg host, usually 10 to 15 mg/kg host. Following the operation, the initial dosage will usually be continued on a daily basis for a period of 1 to 3 weeks, usually 1 to 2 weeks. The dosage may then be tapered to a maintenance dosage of 3 to 10 mg/kg per day, usually 3 to 6 mg/kg per day. The rate at which the dosage is tapered to the maintenance level may range from 3 to 8% per week and will usually be about 5%/week. The dosage will typically be adjusted based on trough blood levels to maintain a concentration of 150 to 250 µg/ml, as measured by HPLC, RIA, ELISA or Tdx assay. The subject formulations may be administered in conjunction with additional agents, where adjunct therapy is recommended and is known in the art. For example, the subject formulations may be administered in conjunction with adrenal corticosteroids and azathioprine.

Administration of the subject formulations in conjunction with transplantation of a donor organ to a host will result in a prolongation of the viability of the donor organ in the host as a result of suppression of the host's immune response to the presence of the donor organ. By "prolongation of viability" is meant that the donor organ remains viable in the host for a longer period of time than it would have had immunosuppressive therapy not been employed in conjunction with the transplantation. Thus, prolongation of viability includes maintenance of viability for an indefinite period of time. A donor organ is considered viable as long as it maintains functionality in the host environment.

The following examples are offered by way of illustration and not by way of limitation.

EXPERIMENTAL

The following oral Cyclosporin A formulations were prepared. In each case, 100 mg CsA, the indicated amount of surfactant, and the indicated amount of ethanol or propylene glycol were added to a 1.0 ml volumetric flask, and the final volume of 1.0 ml was achieved by addition of a suitable volume of fatty acid ester.

| Formulation | Composition | | |
|---|---|---|---|
| 19 | EtOH | 0.1 ml | (10%) |
|  | Tween 80 | 300 mg | (0.278 ml) |
|  | IM | q.s. to 1.0 ml | (0.622 ml) (531 mg) |
| 20 | EtOH | 0.05 ml | (5%) |
|  | Brij 30 | 350 mg | (0.368 ml) |
|  | IM | q.s. to 1.0 ml | <(0.582 ml)(496 mg) |

-continued

| Formulation | Composition | | |
|---|---|---|---|
| 21 | PG | 0.05 ml | (5%) |
|  | Brij 30 | 350 mg | (0.368 ml) |
|  | IM | q.s. to 1.0 ml | <(0.582 ml)(496 mg) |
| 22 | EtOH | 0.1 ml | (10%) |
|  | Tween 80 | 300 mg | (0.278 ml) |
|  | EO | q.s. to 1.0 ml | <(0.622 ml)(541 mg) |
| 23 | EtOH | 0.05 ml | (5%) |
|  | Brij 30 | 350 mg | (0.368 ml) |
|  | EO | q.s. to 1.0 ml | <(0.582 ml) (506 mg) |
| 24 | PG | 0.05 ml | (5%) |
|  | Brij 30 | 350 mg | (0.368 ml) |
|  | EO | q.s. to 1.0 ml | <(0.582 ml) (506 mg) |
| 33 | EtOH | 0.1 ml | (10%) |
|  | Brij 30 | 150 mg | (0.158 ml) |
|  | IM | q.s. to 1.0 ml | <(0.742 ml)(633 mg) |
| 34 | EtOH | 0.1 ml | (10%) |
|  | Brij 30 | 150 mg | (0.158 ml) |
|  | EO | q.s. to 1.0 ml | <(0.742 ml)(646 mg) |
| 35 | EtOH | 0.1 ml | (10%) |
|  | Tween 80 | 500 mg | (0.463 ml) |
|  | PG | q.s. to 1.0 ml | <(0.437 ml)(453 mg) |
| 36 | EtOH | 0.1 ml | (10%) |
|  | Tween 80 | 300 mg | (0.278 ml) |
|  | PG | 100 mg | (0.097 ml) |
|  | EO | q.s. to 1.0 ml | <(0.525 ml)(465 mg) |
| 37 | EtOH | 0.1 ml | (10%) |
|  | Tween 80 | 300 mg | (0.278 ml) |
|  | PEG 400 | 100 mg | (0.088 ml) |
|  | EO | q.s. to 1.0 ml | <(0.534 ml)(464 mg) |
| 38 | EtOH | 0.1 ml | (10%) |
|  | Brij 30 | 300 mg | (0.316 ml) |
|  | PG | 100 mg | (0.097 ml) |
|  | EO | q.s. to 1.0 ml | <(0.487 ml)(424 mg) |
| 39 | EtOH | 0.1 ml | (10%) |
|  | Brij 30 | 300 mg | (0.316 ml) |
|  | PG | 200 mg | (0.193 ml) |
|  | EO | q.s. to 1.0 ml | <(0.391 ml)(340 mg) |
| 40 | PG | 300 mg | (290 ml) |
|  | Brij 30 | 300 mg | (0.316 ml) |
|  | EO | q.s. to 1.0 ml | <(0.394 ml)(343 mg) |
| 41 | EtOH | 0.05 ml | (5%) |
|  | Brij 30 | 150 mg | (0.158 ml) |
|  | Tween 80 | 100 mg | (0.093 ml) |
|  | EO | q.s. to 1.0. ml | <(0.649 ml) (565 mg) |
| 42 | PG | 0.05 ml | (5%) |
|  | Brij 30 | 150 mg | (0.158 ml) |
|  | Tween 80 | 100 mg | (0.093 ml) |
|  | EO | g.s. to 1.0. ml | <(0.649 ml) (565 mg) |

PG = Propylene Glycol
EtOH = ethanol
Brij 30 = polyoxyethylene (4) lauryl ether
Tween 80 = polyoxyethylene (20) mono sorbitan mono-oleate
IM = isopropyl myristate
EO = ethyl oleate The pharmacokinetic properties of cyclosporin in each of the above formulations was studied as follows. For each of the above formulations, the following pharmacokinetic parameters were determined: (a) the peak blood concentration of cyclosporin ($C_{max}$); (b) time required to attain $C_{max}$ ($T_{max}$); and the area under the curve time-profile (AUC). For each of the above formulations, as well as a SANDIMMUNE® Oral Solution (SO), CsA-naive Sprague Dawley rats weighing 250–350 gm were fed pelletized standard food (Agway® 3000, Granville Mill, Greensboro, N.C.) and water ad libitum. One day prior to the experiment, silicone rubber cannulae were inserted into the right jugular and right femoral veins under light ether anesthesia. After overnight fast, CsA was administered by gavage.

Following administration, blood samples, 200 µl each, were collected from the jugular vein in 0.5 ml polypropylene microfuge tubes containing 0.3 mg of lyophilized Na EDTA and vortexed immediately for 10 sec. The sampling times for animal subjected to oral formulations were 0, 0.5, 1, 2, 4, 8, 12, 24, 36, 48 and 72 hr after administration.

CsA, including some of its metabolites, was determined in whole blood by fluorescent polarization immunoassay (FPI) (Tdx, Abbot Lab.). Briefly, 150 µl of the whole blood sample were quantitatively transferred to a 1.5 ml microfuge tube. Cells were lysed and dissolved with 50 µl of a surfactant-containing solubilizing reagent. Proteins are then precipitated out with 300 µl of acetonitrile. After centrifugation, the supernatant was subjected to the FPI assay in a TDx Autoanalyzer following the procedure recommended by Abbott Diagnostics. Since the TDx assay was originally developed for human blood, some of the recommended procedures were modified as follows. A series of standard solutions of known CsA concentration were prepared by adding a known amount of CsA to rat blood treated with EDTA. When the CsA concentration in a sample was expected to be greater than 1.0 µg/ml, the blood sample was diluted 10-fold in a 0.1 M-phosphate buffer at pH 7.0. For diluted samples, another calibration curve was made using a series of standard solutions containing known amounts of CsA, which is volume-wise 10% in rat blood and 90% phosphate buffer.

Descriptive pharmacokinetic parameters were obtained from non-compartmental analyses. The peak concentration ($C_{max}$) and the time at which the peak concentration occurred ($T_{max}$) were estimated by inspection of the raw concentration-time profile for each rat. The area under the concentration-time profile (AUC) from time 0 through the last data point ($AUC_{0-t}$) was calculated according to the linear trapezoidal procedure. The residual area under the tail of the concentration-time profile ($AUC_{t-\infty}$) was estimated as the ratio of the final observed concentration (C*) to the first-order rate constant associated with the terminal elimination phase of the concentration-time profile ($\lambda_z$). The rate contact $\lambda_z$ was determined by log-linear regression of the concentration-time data in the apparent terminal log-linear phase of the concentration-time profile (i.e., the final 3 to 5 data points, depending on the profile under analysis). The total AUC ($AUC_{t-\infty}$) was taken as the sum of $AUC_{0-t}$ and $AUC_{t-\infty}$.

Figure 2:
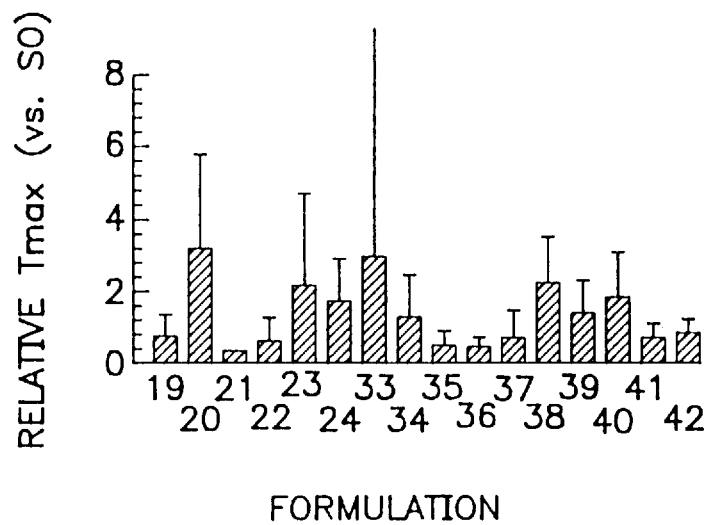
FIG. 2 provides the time at which $C_{max}$ occurred ($T_{max}$) for each of formulations shown in FIG. 1, where $T_{max}$ is provided as relative value compared to the $T_{max}$ of SANDIMMUNE ORAL formulation (SO).
Figure 3:
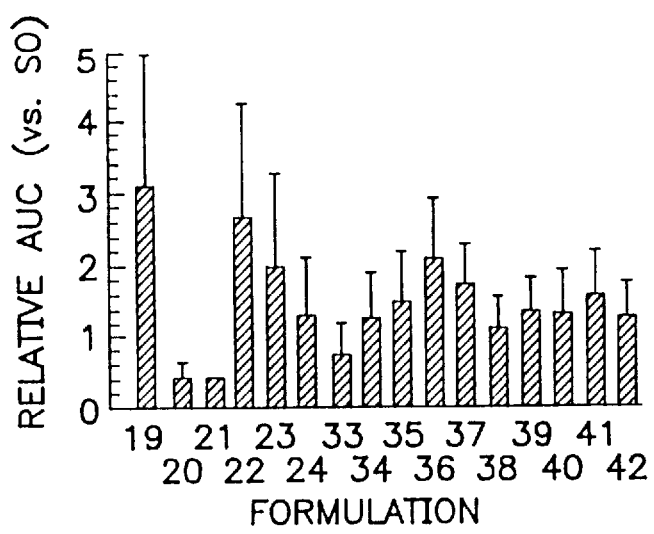
FIG. 3 provides the relative area under concentration-time profile (AUC) for each of the formulations shown in FIG. 1, where AUC is provided as a relative value compared to the AUC value for SANDIMMUNE ORAL formulation (SO).

The results for each formulation were compared with the results obtained for SO, and are provided in FIGS. 1–3.

From the above results and discussion, it is evident that novel cyclosporin formulations having high bioavailability are provided. The subject formulations are capable of comprising high concentrations of cyclosporin. The subject formulations are amenable to delivery in capsule form, including hard capsule form, providing for ease of storage and handling.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An oral cyclosporin formulation consisting essentially of:
   cyrlosporin;
   at least one alkanol of from 2 to 3 carbon atoms;
   at least one non-ionic polyoxyethylene surfactant, wherein said surfactant is selected from the group consisting of polyoxyethylene ether and fatty acid monoesters of ethoxylated polyols of from 4 to 6 carbon atoms; and
   an ester of a lower alkanol and a fatty acid of from 14 to 18 carbon atoms.

2. The oral formulation according to claim 1, wherein said Cyclosporin A is present in said formulation in a range of from about 50 to 150 mg/ml.

3. The oral formulation according to claim 1, wherein said at least one alkanol is from about 5 to 35% (v/v) of said formulation.

4. The oral formulation according to claim 1, wherein said at least one non-ionic polyoxyethylene surfactant is from about 5 to 50% (v/v) of said formulation.

5. The oral formulation according to claim 1, wherein said fatty acid ester is from about 35 to 80% (v/v) of said formulation.

6. An oral cyclosporin formulation consisting essentially of:
   Cyclosporin A at a concentration ranging from about 50 to 150 mg/ml;
   at least one alkanol selected from the group consisting of ethanol and propylene glycol, wherein said at least one alkanol is from about 5 to 35% (v/v) of said formulation;
   at least one non-ionic polyoxyethylene surfactant, wherein said non-ionic surfactant is selected from the group consisting of a polyoxyethylene ether and a mono-ester of an ethoxylated sorbitol, and is from about 5 to 50% (v/v) of said formulation; and
   an ester of a lower alkanol of from 2 to 4 carbon atoms and a fatty acid of from 14 to 18 carbon atoms, wherein said fatty acid ester is from about 35 to 80% (v/v) of said formulation.

7. The formulation according to claim 6, wherein said non-ionic surfactant is selected from the group consisting of polyoxyethylene (4) lauryl ether and polyoxyethylene (20) mono sorbitan mono-oleate.

8. An oral cyclosporin formulation consisting essentially of:
   Cyclosporin A at a concentration ranging from about 50 to 150 mg/ml;
   at least one alkanol selected from the group consisting of ethanol and propylene glycol, wherein said at least one alkanol is from about 5 to 35% (v/v) of said formulation;
   at least one non-ionic polyoxyethylene surfactant, wherein said non-ionic surfactant is selected from the group consisting of a polyoxyethylene ether and a mono-ester of an ethoxylated sorbitol, and is from about 5 to 50% (v/v) of said formulation; and
   a fatty acid ester selected from the group consisting of isopropyl myristate and ethyl oleate, wherein said fatty acid ester is from about 35 to 80% (v/v) of said formulation.

9. The formulation according to claim 6 wherein said formulation is present in a hard capsule.

10. An oral, hard capsule cyclosporin formulation consisting essentially of:
    a hard capsule;
    Cyclosporin A at a concentration ranging from about 50 to 150 mg/ml;
    an alkanol selected from the group consisting of propylene glycol and ethanol, wherein said alkanol is from about 5 to 15% (v/v) of said formulation;

a non-ionic polyoxyethylene surfactant selected from the group consisting of polyoxyethylene (4) lauryl ether and polyoxyethylene (20) mono sorbitan mono-oleate, wherein said surfactant is from about 10 to 40% (v/v) of said formulation; and a fatty acid ester selected from the group consisting of isopropyl myristate and ethyl oleate, wherein said fatty acid ester is from about 35 to 80% (v/v) of said formulation.

11. An oral, hard capsule cyclosporin formulation consisting essentially of:

a hard capsule;

Cyclosporin A at a concentration ranging from about 50 to 150 mg/ml;

5 to 10% (v/v) ethanol;

a non-ionic polyoxyethylene surfactant selected from the group consisting of polyoxyethylene (4) lauryl ether and polyoxyethylene (20) mono sorbitan mono-oleate, wherein said surfactant is from about 10 to 40% (v/v) of said formulation; and a fatty acid ester selected from the group consisting of isopropyl myristate and ethyl oleate, wherein said fatty acid ester is from about 35 to 80% (v/v) of said formulation.

12. An oral cyclosporin formulation consisting essentially of:

Cyolosporin A at a concentration ranging from about 50 to 150 mg/ml;

from 5 to 10% (v/v) ethanol;

from 45 to 50% (v/v) propylene glycol; and at least one non-ionic polyoxyethylene surfactant wherein said surfactant is selected from the group consisting of polyoxyethylene ethers and fatty acid monoesters of ethoxylated polyols of from 4 to 6 carbon atoms and is from about 45 to 50% (v/v) of said formulation.

13. A method for achieving immunosuppression in a host, said method comprising:

administering to said host an oral cyclosporin formulation consisting essentially of:

Cyclosporin A;

at least one alkanol of from 2 to 3 carbon atoms;

at least one non-ionic polyoxyethylene surfactant, wherein said surfactant is selected from the group consisting of polyoxyethylene ethers and fatty acid monoesters of ethoxylated polyols of from 4 to 6 carbon atoms; and an ester of a lower alkanol and a fatty acid of from 14 to 18 carbon atoms;

whereby immunosuppression in said host is achieved.

14. The method according to claim 13, wherein said Cyclosporin A is present in said formulation in a range of from about 50 to 150 mg/ml.

15. The method according to claim 13, wherein said alkanol is selected from the group consisting of ethanol and propylene glycol and is from about 5 to 35% (v/v) of said formulation.

16. The method according to claim 13, wherein said non-ionic polyoxyethylene surfactant is selected from the group consisting of polyoxyethylene (4) lauryl ether and polyoxyethylene (20) mono sorbitan mono-oleate.

17. The method according to claim 13, wherein said fatty acid ester is selected from the group consisting of isopropyl myristate and ethyl oleate and is from about 35 to 80 % (v/v) of said formulation.

18. A method for prolonging the viability of a donor organ in a host, said method comprising;

administering to said host in conjunction with transplantation of said donor organ an oral cyclosporin formulation consisting essentially of:

Cyclosporin A in a range from about 50 to 150 mg/ml;

an alkanol in a range from about 5 to 35% (v/v) selected from the group consisting of ethanol and propylene glycol;

a non-ionic surfactant in a range from about 5 to 50% (v/v) selected from the group consisting of polyoxyethylene (4) lauryl ether and polyoxyethylene (20) mono sorbitan mono-oleate; and a fatty acid ester in a range from about 35 to 80% (v/v) selected from the group consisting of isopropyl myristate and ethyl oleate;

whereby the viability of said donor organ in said host is prolonged.

19. The method according to claim 16, wherein said oral formulation is administered in a hard capsule.

20. The method according to claim 15, wherein said oral formulation is administered chronically after said transplantation.

* * * * *

UNITED STATES PATENT AND TRADEMARK OFFICE
CERTIFICATE OF CORRECTION

PATENT NO. : 5,834,017
DATED : November 10, 1998
INVENTOR(S) : CHO et al.

It is certified that error appears in the above-identified patent and that said Letters Patent is hereby corrected as shown below:

Second inventor, delete "F." and insert therefore --E.--.

Under Attorney, Agent, or Firm, delete "Honbach", and insert therefore --Hohbach--.

Page 2 of references cited, fourth document under Other Publications, delete "rate" and insert therefore --rat--.

Column 3, line 43, delete "BRU 30®" and insert therefore --BRIJ 30®--.

Column 7, line 64, delete "cyrlosporin" and insert therefore --cyclosporin--.

Column 8, line 4, delete "an ester" and insert therefore --a monoester--.

Column 8, line 16, delete "fatty acid ester" and insert therefore --fatty acid monoester--.

Column 8, line 32, delete "an ester" and insert therefore --a monoester--.

Column 8, line 34, delete "fatty acid ester" and insert therefore --fatty acid monoester--.

Column 8, line 58, delete "to claim 6" and insert therefore --to any of Claims 6, 8, or 12,--.

UNITED STATES PATENT AND TRADEMARK OFFICE
CERTIFICATE OF CORRECTION

PATENT NO. : 5,834,017
DATED : November 10, 1998
INVENTOR(S) : CHO et al.

It is certified that error appears in the above-identified patent and that said Letters Patent is hereby corrected as shown below:

Column 10, line 3, delete "an ester" and insert therefore --a monoester--.

Column 10, line 18, delete "fatty acid ester" and insert therefore --fatty acid monoester--.

Column 10, line 35, delete "fatty acid ester" and insert therefore --fatty acid monoester--.

Signed and Sealed this

Sixth Day of April, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT : 5,834,017

DATED : November 10, 1998

INVENTOR(S) : Moo J. Cho et al

It is certified that error appears in the above-identified patent and that said Letters Patent is hereby corrected as shown below:

On the title page, item [73] Assignee, should read as follows:

--[73] Assignee: SangStat Medical Corporation, Menlo Park, Calif. and University of North Carolina at Chapel Hill, Chapel Hill, N.C.--.

Signed and Sealed this

Thirtieth Day of May, 2000

*Attest:*

Q. TODD DICKINSON

*Attesting Officer*     *Director of Patents and Trademarks*